United States Patent
Thys (10) Patent No.: US 10,610,631 B2
(45) Date of Patent: Apr. 7, 2020

(54) METHOD FOR REMOVING BLOOD FROM AN EXTRACORPOREAL BLOOD CIRCUIT UNDER PRESSURE CONTROL AND APPARATUSES

(71) Applicant: Fresenius Medical Care Deutschland GmbH, Bad Homburg (DE)

(72) Inventor: Martin Thys, Gärtringen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 387 days.

(21) Appl. No.: 15/304,163

(22) PCT Filed: Apr. 16, 2015

(86) PCT No.: PCT/EP2015/058298
§ 371 (c)(1),
(2) Date: Oct. 14, 2016

(87) PCT Pub. No.: WO2015/158843
PCT Pub. Date: Oct. 22, 2015

(65) Prior Publication Data
US 2017/0189602 A1 Jul. 6, 2017

(30) Foreign Application Priority Data
Apr. 16, 2014 (DE) .................. 10 2014 105 473

(51) Int. Cl.
*A61M 1/36* (2006.01)
*A61M 1/16* (2006.01)
*A61M 1/34* (2006.01)
*A61M 39/28* (2006.01)

(52) U.S. Cl.
CPC ........ *A61M 1/3639* (2013.01); *A61M 1/1621* (2014.02); *A61M 1/3424* (2014.02);
(Continued)

(58) Field of Classification Search
CPC .............. A61M 1/1621; A61M 1/3424; A61M 1/3626; A61M 1/3639; A61M 1/3643;
(Continued)

(56) References Cited

U.S. PATENT DOCUMENTS

| | | | |
|---|---|---|---|
| 2010/0274168 A1 | 10/2010 | Gronau et al. | |
| 2011/0071465 A1* | 3/2011 | Wang | A61M 1/28 604/67 |
| 2013/0030346 A1* | 1/2013 | Gronau | A61M 1/3643 604/6.09 |

FOREIGN PATENT DOCUMENTS

| | | |
|---|---|---|
| DE | 102009027195 | 12/2010 |
| EP | 2 535 065 | 12/2012 |

(Continued)

OTHER PUBLICATIONS

English translation of IPRP from PCT2015/058298 (Oct. 18, 2016).*
(Continued)

*Primary Examiner* — Benjamin J Klein
(74) *Attorney, Agent, or Firm* — Fish & Richardson P.C.

(57) ABSTRACT

A method of removing blood from an extracorporeal blood circuit and/or a functional device, each of which is connectable or connected with a blood treatment apparatus for the purpose of a blood treatment of a patient, after concluding a blood treatment session, the method comprising operating a blood pump in a second conveying direction which is opposite to a first conveying direction of the blood pump which is customary during the blood treatment, and an arterial line section of the extracorporeal blood circuit is or will be connected with a venous line section of the extracorporeal blood circuit.

17 Claims, 2 Drawing Sheets

(52) U.S. Cl.
CPC ........ *A61M 1/3626* (2013.01); *A61M 1/3643* (2013.01); *A61M 1/3644* (2014.02); *A61M 1/3656* (2014.02); *A61M 39/28* (2013.01); *A61M 1/3646* (2014.02); *A61M 2205/12* (2013.01); *A61M 2205/18* (2013.01); *A61M 2205/3306* (2013.01); *A61M 2205/3331* (2013.01); *A61M 2205/3334* (2013.01); *A61M 2205/3337* (2013.01); *A61M 2205/50* (2013.01)

(58) Field of Classification Search
CPC .............. A61M 1/3644; A61M 1/3646; A61M 1/3656; A61M 39/28; A61M 2205/12; A61M 2205/18; A61M 2205/3306; A61M 2205/3331; A61M 2205/3334; A61M 2205/3337; A61M 2205/50
See application file for complete search history.

(56) References Cited

FOREIGN PATENT DOCUMENTS

| | | |
|---|---|---|
| EP | 2 535 067 | 12/2012 |
| JP | 2010184029 | 8/2010 |
| JP | 2012-524563 | 10/2012 |
| WO | 2013/017240 | 2/2013 |

OTHER PUBLICATIONS

International Search Report; International Application No. PCT/EP2015/058298; dated Jun. 25, 2015; 6 pages.
International Preliminary Report on Patentability in Application No. PCT/EP2015/058298, dated Oct. 18, 2016, 8 pages.

* cited by examiner

METHOD FOR REMOVING BLOOD FROM AN EXTRACORPOREAL BLOOD CIRCUIT UNDER PRESSURE CONTROL AND APPARATUSES

CLAIM OF PRIORITY

This application is a national stage of and claims priority under 35 U.S.C. § 371 to International Application No. PCT/EP2015/058298, filed Apr. 16, 2015, which claims priority to German Application No. 10 2014 105 473.3, filed Apr. 16, 2014, the entire contents of which are hereby incorporated by reference.

TECHNICAL FIELD

The present invention relates to methods of removing blood from an extracorporeal blood circuit and to related blood treatment apparatuses.

BACKGROUND

Not least for hygienic reasons, blood remaining in the blood circuit is regularly removed from the extracorporeal blood circuit after use of the latter.

Certain aspects of the present invention relate to methods of removing blood from an extracorporeal blood circuit or from a functional device after the conclusion of a blood treatment session.

Other aspects of the present invention relate to a blood treatment apparatus, a control unit, a suitable digital storage medium, a suitable computer program product, and a suitable computer program for executing methods of removing blood from an extracorporeal blood circuit.

SUMMARY

Advantages achievable by methods according to aspects the present invention may in certain embodiments also be achieved by apparatuses according to other aspects of the present invention.

In certain aspects of the present invention, a method is suited and intended for removing blood from an extracorporeal blood circuit which comprises at least one arterial line section and at least one venous line section, and/or for removing blood from a functional device which is or are connectable or connected with a blood treatment apparatus for the purpose of a blood treatment of a patient, or each from sections hereof.

The method encompasses conveying the fluid present in the extracorporeal blood circuit after the conclusion of the treatment using a blood pump which was already being used for the blood treatment. While the blood pump has conveyed fluid in a first conveying direction during the blood treatment, in the method according to certain embodiments of the present invention conveying takes place by operating the blood pump in a second conveying direction which is opposite to the first conveying direction. For executing the method according to certain embodiments of the present invention, a first section of the arterial line section is or will be connected with a second section of the venous line section of the extracorporeal blood circuit.

Thereby, the feed rate of the blood pump in certain embodiments is or will be adapted, at least at a certain point or during at least a period of time continuously or until reaching the pre-determined maximum value of the feed rate to which the feed rate of the blood pump is limited, to be between 75% and 90%, preferably between 80% and 84%, particularly preferred is 82% of the feed rate of a second conveying device of the employed blood treatment apparatus.

This may take place optionally under reserve taking into consideration a specified limitation.

The blood treatment apparatus that is employed for executing the method according to certain embodiments of the present invention comprises next to the blood pump at least a second conveying device, in particular a substitute pump for bringing a second fluid, in particular a substitute fluid, into the interior of a line of the extracorporeal blood circuit and/or for the conveyance of a line contents inside of the line interior of the extracorporeal blood circuit.

The blood treatment apparatus is provided and embodied and/or equipped for executing the method described herein.

The control unit is suitable and provided and/or arranged and/or configured for executing the method described herein in interaction with each required device thereto, as described in the following by way of example.

A digital, particularly a non-volatile storage medium, particularly in the form of a machine-readable data storage device, particularly in the form of a disk, CD, EPROM or DVD, with electrically readable control signals may interact with a programmable computer system such that the mechanical steps of the method described herein are prompted.

In doing so, all or some of the mechanically executed steps of the method may be prompted.

A computer program product comprises a program code that is volatile or saved on a machine-readable medium for prompting the mechanical steps of the method described herein when the computer program product runs on a computer. According to certain embodiments of the present invention a computer program product can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

The term machine-readable medium as used herein denotes in certain embodiments of the present invention a medium containing data or information which is interpretable by software and/or hardware. The medium may be a data medium, like a disk, a CD, DVD, a USB stick, a flashcard, an SD card or the like.

A computer program according to certain aspects of the present invention comprises a program code for prompting the mechanical steps of the method described herein when the computer program runs on a computer. A computer program can be understood as, for example, a physical, ready-for-distribution software product which comprises a computer program.

It also applies for the computer program product and the computer program that all or some of the mechanically executed steps of the method described herein are prompted.

Embodiments may comprise some or all of the following features in combination as long as this is not realized by the skilled person to be technically impossible.

In all of the following embodiments, the use of the expression may be or may have and so on, is to be understood synonymously with preferably is or preferably has, respectively, and so on, and is intended to illustrate exemplary embodiments.

Whenever a numerical word is mentioned herein, the skilled person understands this as an indication of a numerically lower limit. As long as it does not lead to any discernible contradiction for the skilled person, the skilled person, therefore, implicitly reads for example in the indication "one" at all times "at least one". This understanding is also encompassed by the present invention as well as the interpretation that, for example, "one" can alternatively be meant as "exactly one", as long as this is technically possible in the view of the skilled person. Both of which are encompassed by the present invention and apply to all used numerical words herein.

In some exemplary embodiments, a feed rate of the blood pump is limited, particularly by the user, to a pre-determined value, preferably to a value between 90 and 110 ml/min.

The extracorporeal blood circuit is in certain embodiments a tube set. In any case, the extracorporeal blood circuit is provided for extracorporeally conducting blood of a patient, e.g., during hemodialysis, hemofiltration, hemodiafiltration or the like.

In some embodiments, the extracorporeal blood circuit is at least in sections embodied as an integral and, where appropriate, permanent part of the functional device, in others it is not. A freely movable tube section of the extracorporeal blood circuit may therefore continue in one piece or integrally on or in the functional device, e.g., a blood cassette, and vice versa.

A functional device is in certain embodiments a device which is used in a blood treatment. Examples of functional devices include internal and external functional devices, medical disposables, in particular blood cassettes such as a disposable blood cassette, or other blood-conducting devices.

Exemplary embodiments of a blood cassette are in particular disclosed in the application of the Applicant with the publication number DE 10 2009 018 664 A1 having the title Externe Funktionseinrichtung, Blutbehandlungsvorrichtung zum Aufnehmen einer erfindungsgemäßen externen Funktionseinrichtung, sowie Verfahren, which was submitted to the German Patent and Trademark Office on 23 Apr. 2009, and in the application of the Applicant with the publication number DE 10 2009 024 468 A1 of the same title, which was submitted to the German Patent and Trademark Office on 10 Jun. 2009. The respective disclosures are herewith fully incorporated by way of reference.

In certain embodiments, the functional device as external functional device is not a part of the blood treatment apparatus, i.e. not an integral element thereof. In other embodiments, the functional device may be a part of the blood treatment apparatus.

A blood treatment apparatus is provided and/or embodied for performing or prompting a medical treatment, in particular a blood treatment of the patient, e.g., a dialysis. For this purpose, the blood treatment apparatus is connected with or comprises at least one extracorporeal blood circuit which comprises a line interior.

The arterial line section of the extracorporeal blood circuit is in certain embodiments the line section in which the patient blood that leaves the body of the patient for the purpose of the extracorporeal blood treatment flows and in which it is present before it enters the blood treatment device, e.g., a dialyzer.

In certain embodiments, the first section of the arterial line section is or encompasses the arterial needle connection to the patient, e.g. the arterial needle connection in a double-needle dialysis method.

The venous line section of the extracorporeal blood circuit is in some embodiments the line section from which the extracorporeally treated patient blood flows towards or back into the body of the patient after its treatment in a blood treatment device, e.g., a dialyzer.

In certain embodiments, the second section of the venous line section is or encompasses a venous port, for example a venous addition port or a venous addition point. It may, where appropriate, be used or provided for the addition of substituate liquid, calcium citrate heparin or the like to the patient blood flowing in the line section of the extracorporeal circuit.

In certain embodiments, the venous addition point of the venous line section of the extracorporeal blood circuit leads, optionally directly or indirectly, into the venous line section upstream from a blood chamber and upstream from a clot catcher.

In some embodiments, the venous addition point is an integral part of a blood cassette.

The blood treatment apparatus comprises a blood pump for conveying blood within the line interior of the extracorporeal blood circuit.

In certain embodiments, the first conveying direction—as customary during the blood treatment—corresponds to a conveying direction from an arterial access (blood withdrawal point) of a patient to a blood treatment device, for example a blood filter or a dialyzer and subsequently through the venous line section of the extracorporeal circuit to the venous access (blood return point).

The second conveying direction which is opposite to the first conveying direction therefore proceeds in such embodiments from venous to arterial.

"Removing blood" denotes in certain embodiments completely—or basically or nearly completely- or partially removing blood from an extracorporeal blood circuit after conclusion of a blood treatment session.

Reinfusing the blood removed from the extracorporeal blood circuit into the vascular system of the patient itself is in some embodiments not a part of the method, in others however, it is.

The blood treatment apparatus comprises at least one second conveying device. The second conveying device serves to introduce at least a second fluid which is different from the blood, for example a substituate liquid, into the line interior of the extracorporeal blood circuit and/or to convey the fluid herein.

Introducing the second fluid, hereafter simply—but not restrictively—denoted as substituate liquid, into the line interior of the extracorporeal blood circuit by operating the second conveying device, hereafter simply—but not restrictively—denoted as substituate pump, takes place in certain embodiments after connecting the first section of the arterial line section with the second section of the venous line section.

In some embodiments, the blood pump is operated in the second conveying direction such that the flow of the substituate liquid which is introduced into the line interior of the extracorporeal blood circuit is separated into at least a first and a second partial flow. The first partial flow of the substituate liquid moves towards a blood treatment device, and the second partial flow of the substituate liquid moves into the second conveying direction.

In certain embodiments, the method encompasses disconnecting the first section.

In some embodiments, the method encompasses connecting the first section with a venous addition point of the venous line section of the extracorporeal blood circuit or with a venous addition point of the functional device (for example the blood cassette).

In certain embodiments, the second conveying device and the blood pump are started, in particular basically or nearly or completely, at the same time.

The feed rates of the second conveying device and the blood pump in some embodiments are or will be set such that a section of the venous line section, e.g., from a pre-dilution point or from a pre-dilution valve to the venous addition point or to a point at which fluid from the venous line section and fluid from the arterial line section are joined or meet, are not emptied of blood before a section of the arterial line section, e.g., until its connection with the venous addition point or up to the point at which fluid from the venous line section is joined with fluid from the arterial line section or both fluids meet.

In certain embodiments, the feed rate of the blood pump is (initially, always, or on average) lower than the feed rate of the second conveying device or is adjusted accordingly.

In some embodiments, the feed rates of the blood pump and/or of the second conveying device are monitored and/or controlled or regulated by pressure monitoring and/or pressure measurement and/or pressure limitation during the removal of the blood.

In some embodiments, the feed rates of the blood pump and the second conveying device during the removal of the blood are monitored and/or controlled or regulated by pressure monitoring and/or pressure measurement and/or pressure limitation, in particular by multiple measurements of an actual feed pressure of the blood pump, for example in a timely connection with the mesh or position or the tilt angle of a roll of a blood pump, as long as it is embodied as a roll pump, by determining the control difference between the measured feed pressure of the blood pump and a target value and by raising the feed rate of the blood pump according to the control difference.

In some embodiments, the actual feed pressure is gripped, measured or calculated when the pre-determined tilt angle or tilt angle area of a pump rotor of the blood pump has been reached.

In some embodiments, the actual feed pressure is measured by the arterial pressure sensor.

In some embodiments, the feed rate of the blood pump and/or the feed rate of the second conveying device are set or limited with the intention to reach a target pressure P_art,target and/or not to exceed it. The target pressure is set according to the formula (I):

$$P\_art,target = a * P\_art,max$$

wherein the following applies:
P_art,target is the pressure measured by an arterial pressure gauge;
a is a constant; it is preferably between 0.85 and 0.95. Particularly preferred is 0.9;
P_art max is a pre-set or pre-determined measurement range limit or a maximum allowable value for the pressure which is measured by an arterial pressure measurement and it is preferably an alarm-release range.

In some embodiments, the method encompasses the increase of the feed rate of the second conveying device according to formula (II):

$$Q5000\_future = Q5000\_actual + ((P\_art,target) - (P\_art,scan)) * b$$

The following applies thereby:
Q5000_future is a future feed rate of the second conveying device which is to specified t_future at a point of time by the formula (II).
Q5000_actual is an actual feed rate of the second conveying device that is at a point of time t_actual, which is to be replaced by Q5000_future and precedes this temporally, wherein t_actual comes before t_future; t_future may be denoted as t(x+1) and t_actual as t(x).
P_art,target is a pre-set or identified target value, which is to be measured as a target value by means of an arterial pressure measurement, it corresponds to a "target value";
P_art,scan is a pressure value which is measured at the arterial pressure measurement during the adapting of the actual feed rate Q5000_actual of the second conveying device; it corresponds therefore to an actual value or to a value P_art,actual; and
b is a constant; it is preferably between 0.10 and 0.15. Particularly preferred is 0.12.

In certain embodiments, the method encompasses the decrease of the feed rate of the second conveying device according to formula (III):

$$Q5000\_future = Q5000\_actual + ((P\_art,target) - (P\_art,scan)) * c$$

wherein the following applies:
Q5000_future is a feed rate of the second conveying device which is to be set henceforth to a point of time t_future;
Q5000_actual is an actual feed rate of the second conveying device that is at a point of time t_actual, which is to be replaced by Q5000_future and preceeds this temporally, wherein t_actual comes before t_future; t_future may be denoted as t(x+1) and t_actual as t(x);
P_art,target is a pre-set target value which is to be measured by the arterial pressure sensor;
P_art,scan is a pressure value which is measured at an arterial pressure measurement during the adapting of the actual feed rate Q5000_actual; and
c is a constant; it is preferably between 0.20 and 0.30. Particularly preferred is 0.24.

In certain embodiments, the feed rate of the second conveying device is determined such that at the venous addition point—or at a point at which fluid from the venous line section is joined with or meets fluid from the arterial line section—blood (from a line) and substitute liquid (from a different line) of the same degree of dilution meet.

In certain embodiments, the intention is to stop the blood pump or reduce its feed speed or feed rate before substitute liquid downstream (with regard to the second conveying direction) reaches the venous addition point or the point at which fluid from the venous line section and fluid from the arterial line section are joined or meet.

This may in certain embodiments advantageously contribute to a stronger and/or improved flushing of the blood treatment device.

The time for stopping the blood pump or for reducing its feed rate is in certain embodiments determined with the aid of the arterial air bubble detector/optical detector (also known as ABD/OD) which is integrated in the extracorporeal blood circuit. This may advantageously increase the accuracy of determination of the time for stopping.

In other embodiments, the method encompasses stopping the second conveying device or reducing the speed or the feed rate of the second conveying device before substitute liquid downstream (with regard to the second conveying direction) reaches the venous addition point or the point at which fluid from the venous line section and fluid from the arterial line section are joined or meet. This may advantageously contribute to a stronger and/or improved flushing of the arterial line section of the extracorporeal blood circuit. The blood pump is further operated in such embodiments, or it is not further operated.

In certain embodiments, the method encompasses checking the connection of the first section, e.g., of the arterial needle connection, of the extracorporeal blood circuit at the venous addition point of the venous line section of the extracorporeal blood circuit (connection test).

In certain embodiments, checking encompasses creating a pressure balance.

In such embodiments the intention may be to stop the blood pump and/or the second conveying device. Further, the intention may be to open or keep the arterial clamp open.

In certain further embodiments, checking encompasses determining a diastolic patient pressure. A minimum value of the diastolic patient pressure may be saved over a time period of, e.g., 2.5 s. Subsequently, a negative pressure is created by operating the blood pump in the first conveying direction, i.e. forwards, wherein the venous clamp is opened or is already open. In certain embodiments, it is defined that the vascular pressure of the patient has to drop by 50 mmHg within a time period of 2.1 s in order for the connection test to be considered as passed. Alternatively, other values for pressure drop and/or times than the ones named here may be considered. If the desired and/or required pressure reduction has not taken place at all or not within the pre-determined time, the connection test may be considered as failed.

In some embodiments, the method encompasses a step for the free rinsing of the pre-dilution valve. For this purpose, the feed rate of the second conveying device is increased, e.g. in a bole manner, e.g. on a short notice, from preferably 0 ml/min until a specified value. This may optionally be 100 ml/min. In addition or alternative to the feed rate with the aforementioned specified values, a specified quantity of the conveyance is conveyed during the free rinsing. This is based on 0 ml/min by way of example. The free rinsing takes place preferably based on 0 ml/min. After reaching the specified value of the feed rate and/or after conveying the specified volume, the feed rate may optionally be dropped to 0 ml/min.

The functional device is in some embodiments embodied as disposable.

In certain embodiments, the venous addition point of the functional device is embodied to create a fluid connection by simply clamping, attaching or screwing together an arterial needle connection or another section of the arterial line section of the extracorporeal blood circuit. A corresponding embodiment and/or corresponding arrangements may be provided.

In some embodiments, the venous addition point of the functional device and the arterial needle connection or another section of the arterial line section of the extracorporeal blood circuit are from the same connector system, e.g., Luer connectors, or female and male connector.

In certain embodiments, the connection geometry of the venous addition point is embodied the same as or corresponds to the connection geometry of an arterial needle by which the extracorporeal blood circuit is connected for its use.

The control device is in some embodiments embodied as a regulating device.

The blood treatment device is in some embodiments embodied as a hemodialysis apparatus or hemofiltration apparatus or hemodiafiltration apparatus.

The blood treatment device comprises in certain embodiments at least one control device.

Some or all embodiments may comprise one, more or all of the advantages named above and/or hereafter.

Certain aspects of the present invention provide a simple and not very elaborate method for removing blood from an extracorporeal blood circuit after a blood treatment session as well as corresponding apparatuses. By removing blood at the end of the treatment, the risk of contamination may advantageously be reduced during further use or disposing of the blood circuit.

During a blood treatment, blood clots may be formed on construction-related unevenness (see reference numeral 33 in FIG. 1) During un utmost precautionary free rinsing, as described herein, the second conveying device conveys such blood clots with a specified free rinsing rate, e.g. by bringing ca. 10 ml volume, from pre-dilution valve in direction of the blood entry filter. Thereby, the pre-dilution valve is liberated from blood clots. Due to the herein described relation between the feed rate of the blood pump and the feed rate of the second conveying device (preferably 82%), it is advantageously guaranteed that such blood clots are not brought in direction of the venous line section until the venous needle, rather, they accumulate at the blood entry side of the blood filter from which, by adapting the aforementioned relation between the feed rate of the blood pump and the feed rate of the second conveying device (preferably 82%), they are not further moved upstream and subsequently they may not reach the venous line section or not even the venous needle and from here further to the vascular system of the patient. This advantageous state is not achievable with other or other precise relations. Moreover, even when the patient due to a user error is mistakenly still connected to the arterial needle during reinfusion, no blood clot may advantageously be infused Furthermore, the venous addition point and the check valve may not be blocked by such blood clots which contributes to a rapid and trouble-free process.

The user may in certain embodiments adjust the maximum flow allowed, desired or determined for removing blood out of an extracorporeal blood circuit at the blood treatment apparatus and does not have to submit any further inputs.

In some embodiments, it is guaranteed due to the proposed regulation that there shall be no exceeding in the measurement range in the arterial pressure sensor. Therefore, the patient and the user are spared the avoidable interruption of the treatment.

In specific embodiments, the greatest possible feed rate via the arterial line section and/or the blood treatment apparatus is conveyed, which contributes to keeping a low sedimentation (and therewith also the remaining blood quantity in the blood filter and/or the extracorporeal blood circuit).

In some of the embodiments, the greatest possible feed rate of the second conveying device is ensured, such that the blood is removed as soon as possible out of the entire blood treatment apparatus.

In specific embodiments, a dynamic control of the feed rate from the blood pump as well as the second conveying device depending on the outcome of the viscosity of the blood and the decreasing viscosity of the increasingly diluted blood during the reinfusion is advantageously possible due to the proposed pressure control.

For functional or constructive requirements, the arterial line section (see reference numeral 1 in FIG. 1) comprises a comparatively low cross section in the area of the venous addition point (reference numeral 7 in FIG. 1) to which it is connected for the reinfusion of blood and/or for emptying the blood filter or the extracorporeal blood circuit. The cross section is needed so that a dosage of medicine may be given as intended (typically for example Q>1 ml/min) through it—and particularly through the venous addition point—Due to the low cross section of the venous addition point, the latter has in comparison with the arterial or venous line section a relatively high flow resistance. For this reason, the use of the apparatus, for example according to WO 2013/017240 A2, for the reinfusion is uncomfortable and/or physically unfavourable. The user would like to prevent the increase of pressure on the pressure sensor until its upper measurement range which may lead to warning the user and to an interruption of the treatment. Therefore, the user shall specify a corresponding low feed rate (typically 70 ml/min.) for the second conveying device. The low feed rate has consequently the disadvantage of a low efficiency of blood return. This is due to fact that at the end of the reinfusion or emptying the blood treatment device, e.g. of the blood filter, more blood rest remains in the blood treatment apparatus. Another disadvantageous consequence of the low feed rate is a sedimentation of the blood within the blood treatment device which again leads to a low efficiency of blood return due to the fact that at the end of the reinfusion or emptying of the blood treatment device, for example of the blood filter, more blood rest remains in the blood treatment device. A further disadvantageous consequence of the low rate is that the procedure of reinfusion takes a long time due to the low feed rate. These disadvantageous consequences do not advantageously occur in some embodiments.

However, also a high feed rate set by the user has disadvantageous consequences in proceeding with the state of the art. As the high feed rate (typically 150 ml/min) leads according to experience to regular alarming due to measurement range excess on the pressure sensor. This makes it necessary for the user to intervene. The process of emptying or reinfusion takes a longer time due to herethrough related interruptions which again leads to sedimentation in the arterial line section and in the blood treatment device. These disadvantages of the state of the art can be prevented by certain embodiments described herein.

In certain embodiments, the method allows for completely returning blood present in the extracorporeal blood circuit at the end of the blood treatment session to the vascular system of the patient via a venous connection with the vascular system of the patient. Infusing substitute liquid or another fluid to the patient at the same time is hereby preventable.

The method may advantageously be implemented in treatment apparatuses already known from practice by a simple-to-perform software update. The blood treatment apparatuses known from practice often already comprise the required machine elements.

BRIEF DESCRIPTION OF DRAWINGS

Hereafter, embodiments of the present invention are exemplarily described with reference to the appended figures. It applies that.

DETAILED DESCRIPTION

Figure 1:
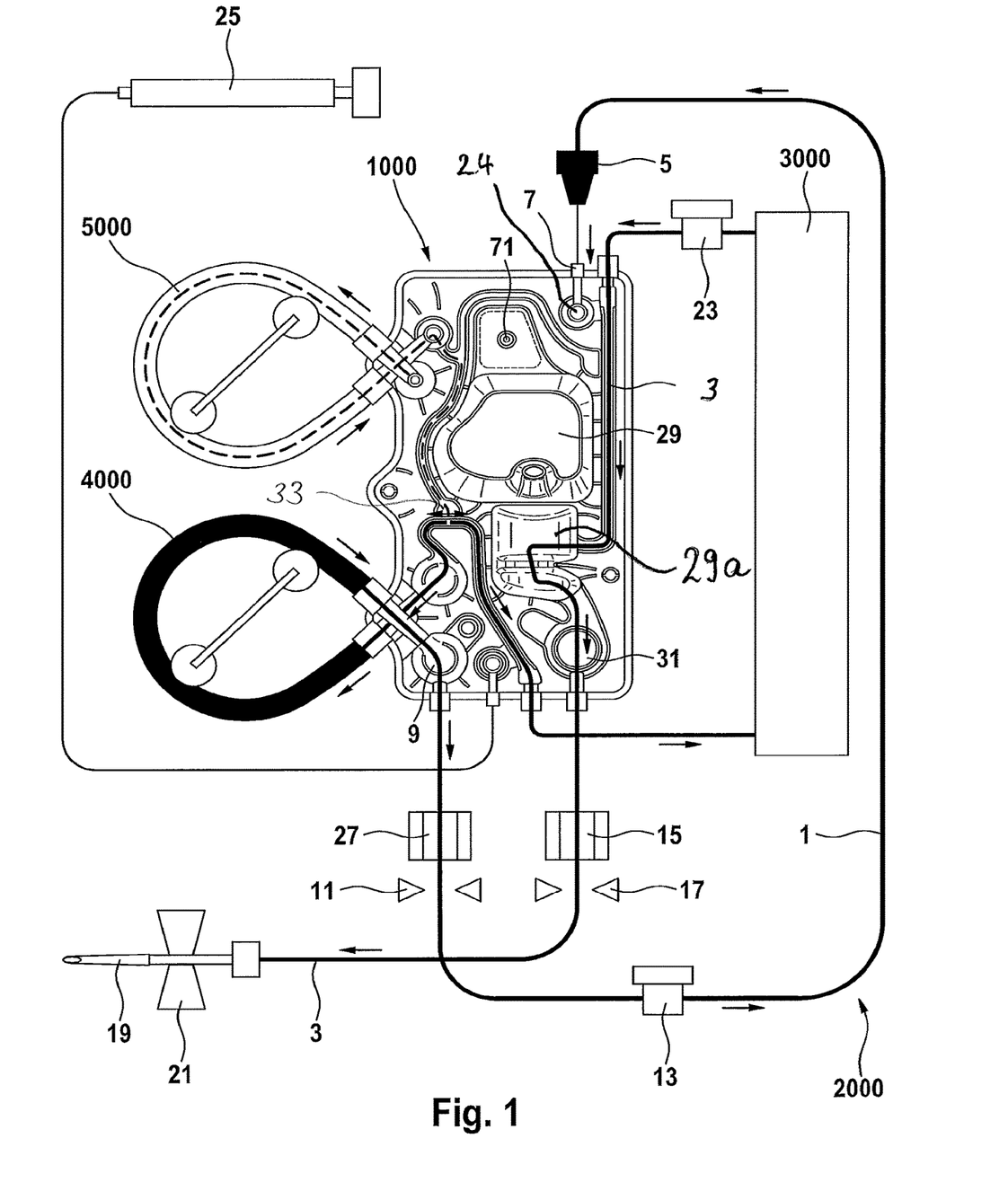
FIG. 1 shows in simplified illustration a medical functional device with an extracorporeal blood circuit, which may be cleared of blood using methods described herein.

FIG. 1 shows a schematically simplified functional device 1000 with an extracorporeal blood circuit 2000 connected herewith.

The extracorporeal blood circuit 2000 comprises or is connected with a blood treatment device 3000, e.g., a blood filter or dialyzer.

A blood treatment apparatus represented in FIG. 1 shows devices used to carry out the methods described herein to automatically completely or mostly reinfuse blood contained in the extracorporeal blood circuit 2000. The blood treatment apparatus comprises a blood pump 4000 and a second conveying device 5000. Both the blood pump 2000 and the second conveying device 5000 convey fluid through sections of the functional device 1000 and of the extracorporeal blood circuit 2000. The functional device 1000 is exemplarily a blood cassette.

Indicated is a connection diagram as well as flow direction, specified by arrows, of blood and substitute (as an example a second fluid) during removal of blood with a simultaneous reinfusion of the blood. The sole double arrow describes a split of the substitute flow in two partial flows The extracorporeal blood circuit 2000 comprises an arterial line section 1 as well as a venous line section 3.

The arterial line section 1 comprises a first section. The first section is in the example of FIG. 1 exemplarily embodied as an arterial needle connection 5.

The venous line section 3 comprises a second section. The second section 3 is embodied in FIG. 1 as a venous addition point 7 of the functional device 1000.

The arterial line section 1 comprises an arterial pressure sensor which is coupled to the functional device 1000 at the location denoted with reference numeral 9 without being itself part of the functional device 1000. This pressure sensor serves, amongst others, to measure the pressure or to determine pressure drop during an optional connections test. It is arranged in the arterial line connection 1 of the extracorporeal blood circuit 2000.

The arterial line section 1 comprises an arterial clamp 11.

The arterial line section 1 comprises an arterial septum 13, here, optionally in the shape of an addition device.

The venous line section 3 comprises a venous air bubble detector/optical sensor 15.

The venous line section 3 comprises a venous clamp 17.

The venous line section 3 comprises a venous needle 19 on a venous patient connector 21.

A venous septum 23, here optionally in the shape of an addition device, is arranged between the blood treatment device 3000 and the location of its connection with the section of the extracorporeal blood circuit 2000 present on the functional device 1000.

The functional device 1000 comprises a check valve 24 which allows a fluid supply in a direction shown by means of an arrow in FIG. 1 through the venous addition point 7 into the functional device 1000 and into the venous line section 3, however it prevents a flow out of the venous line section 3 through the venous addition point out of the functional device 1000.

For adding heparin into the line interior of the extracorporeal blood circuit 2000 during an extracorporeal blood treatment, the extracorporeal blood circuit 2000 is connected with a heparin syringe 25 via a corresponding port of the functional device 1000.

The arterial line section 1 comprises an arterial air bubble detector/optical sensor 27.

During the blood treatment, the extracorporeal blood circuit 2000 is, e.g., as is shown in FIG. 1 in the form of a tube system, connected with the vascular system of the patient via two needles (in the case of a double-needle dialysis). For performing the blood treatment, the extracorporeal blood circuit 2000 is filled with blood of the patient and this blood flows through the extracorporeal blood circuit 2000 during the treatment.

Hereafter, removal of blood from the extracorporeal blood circuit by using the venous addition point 7 of the functional device 1000 is described. In the herein described example of an embodiment of the method being executed by the machine, while removing blood, there is a concurrent reinfusion of this blood.

The method may be started automatically, or manually by the doctor.

For this purpose, in certain embodiments, the arterial patient connector is disconnected from the arterial needle connection 5 after the conclusion of the blood treatment and connected in fluid connection with a port of the blood cassette, here the venous addition point 7. As may be taken from the blood cassette shown in FIG. 1, the venous addition point 7 may lead directly (in other embodiments also indirectly, however) into the venous line section 3 of the extracorporeal blood circuit 2000 upstream from a blood chamber 29 and from a clot catcher 31.

In the example of FIG. 1, the functional device 1000 comprises at the location of the clot catcher 31 or near the latter, in any case downstream thereof, however upstream of the venous air bubble sensor 15, a venous pressure sensor not shown in FIG. 1, which may measure the pressure of the flow of venous blood or fluid passing by. In other embodiments the venous pressure sensor is provided at another suitable location of the functional device 1000 or of the extracorporeal blood circuit 2000.

Figure 2:
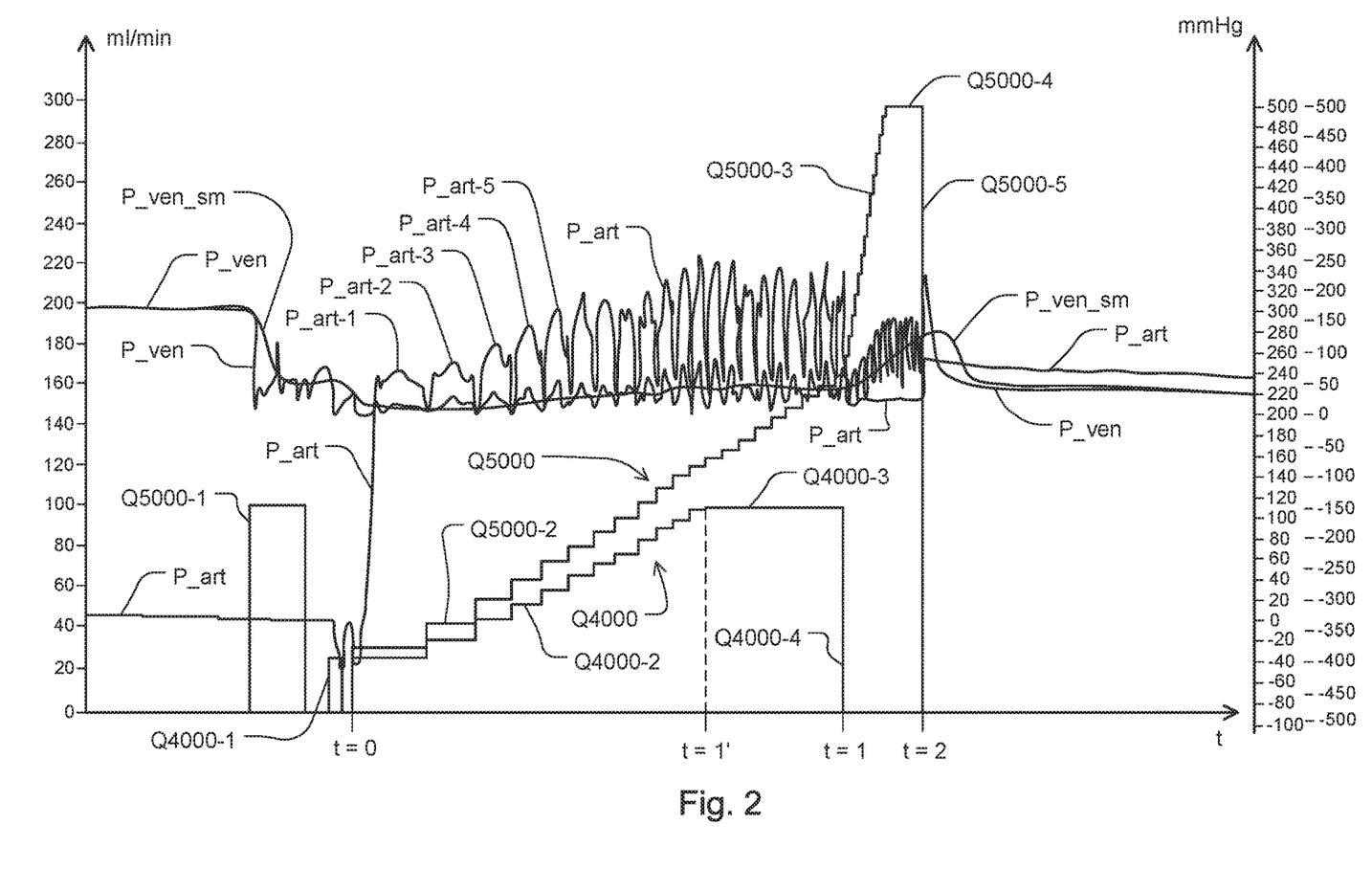
FIG. 2 shows the progress of pressure and volume over a period of time which may occur or that may be measured while performing exemplary embodiments of methods described herein using an arrangement shown in FIG. 1.

The venous addition point 7 is in the above-named applications of the Applicant with the publication numbers DE 10 2009 018 664 A1 and DE 10 2009 024 468 A2 each in FIGS. 1 and 2 marked with the reference numeral 37. The venous addition point 7 is in connection with the venous filter line via a check valve.

The user may be prompted towards the end of the blood treatment to disconnect the arterial needle connection 5 from the arterial patient connector (not shown in FIG. 1) and screw the arterial needle connection 5 onto the Luer connector of the venous addition point 7 of the functional device 1000. In order to check whether the connection is made correctly, a connection test may be performed by the blood treatment apparatus automatically or upon request. In doing so, the correct connection of the arterial line section 1 with the venous line section 3 is checked. Directly conveying the blood via the arterial line section 1 into the vascular system of the patient may therefore advantageously be prevented.

The venous line section 3 is in certain embodiments provided with a check valve, which is why the blood pump 4000 cannot draw in liquid from the venous line section 3 in the first conveying direction. It may therefore be expected that during performance of the connection test the pressure in the arterial line section 1 decreases. If the arterial pressure decreases as expected, it can be assumed that the patient is no longer arterially connected, at least that the (manual) arterial (tube) clamp 11 is closed.

If, as is the case in certain embodiments, an arterial pressure alarm during conveying is provided in this stage of the method, an error would advantageously be detected also early on, even without a connection test. Thus, it may advantageously be possible to forego explicitly testing the connection state.

The connection test for detecting whether the arterial line section 1, e.g., the arterial needle connection 5 of the arterial line section 1, is connected with the venous line section 3, e.g., the venous addition point 7, may hereby take place in detail as described hereafter: At first, a pressure balance is created, wherein the blood pump 4000 and the second conveying device 5000 are stopped. The arterial clamp 11 is open.

Using a pressure sensor 9, the diastolic patient pressure is detected. Hereby, a minimum value is saved over 2.5 s, for example. Subsequently, a negative pressure is built up, whereby the venous clamp 17 is opened and by means of the blood pump 4000 conveyed in the first conveying direction The pressure has to drop because of the check valve 24 below the diastolic patient pressure as detected before, e.g., by 50 mmHg within 2.1 s, otherwise the connection test is considered to be failed.

A predilution valve or predilution connection, provided for introducing substitute liquid into the blood line between the blood treatment device 3000 and the blood pump 4000 is opened for removing blood. The substitute line is connected with the pre-dilution connection, so that the second conveying device 5000 can introduce substituate solution into a section of the extracorporeal blood circuit 2000 which is located between the blood pump 4000 and the blood treatment device 3000.

In the embodiment illustrated here, the blood pump 4000 starts, at the same time (simultaneously) at which conveying begins by means of the second conveying device 5000, conveying backwards, i.e. in the second conveying direction at a lower feed rate than the second conveying device 5000. In doing so, the substitute flow is split due to the different feed speeds of the two pumps—in the example of FIG. 1—one partial flow of the substituate solution moves towards the blood pump 4000, another partial flow of the substituate solution moves in the direction towards the blood treatment device 3000.

The occurring venous and/or arterial pressures are monitored during this process. The set pump rates or feed rates of the conveying devices (blood pump 4000 and second conveying device 5000) may have a considerable effect on the removal of the blood.

In certain embodiments, it is ensured that the feed rate of the blood pump 4000 is not selected to be too high. Thus, it may advantageously be ensured that the blood is not damaged when it flows through the point of introduction—e.g., provided with a thinner tube and a check valve. For this, a limitation of the maximum feed rate, for example based on experience from in vitro tests or in vivo tests, is possible or provided.

In some embodiments, a limitation and/or monitoring the pressure drop across the addition point and/or the addition line and the check valve is possible with the aid of the arterial pressure sensor 9 during reinfusion.

When setting the venous reinfusion rate, i.e. the speed at which the blood that is extracorporeally present is conveyed towards the patient via the venous line section 3 of the extracorporeal blood circuit 2000, it is in some embodiments ensured that the part of the extracorporeal blood circuit 2000 which extends from the pre-dilution point or the pre-dilution valve to the venous addition point is not emptied earlier than or before the arterial line section 1 of the extracorporeal blood circuit 2000 is also emptied.

Hereby, in certain embodiments, a further commingling of blood (arterial) and substitute liquid (venous) and, along with this, an unnecessary increase of the reinfusion volume with the known unpleasant consequences for the patient may advantageously be prevented.

As the volumes of the individual line sections of an extracorporeal blood circuit (also denoted as tube set) are known, it is in certain embodiments of the present invention provided to calculate the maximum possible or permissible venous feed rate as the feed rate in the venous line section of the extracorporeal blood circuit 2000. The calculation may be carried out as described above.

The venous feed rate is in some embodiments set by the feed rate Q5000 of the second conveying device 5000 (substitute pump) deducting the feed rate Q4000 of the blood pump 4000. For this purpose, reference is made to the formulas above.

As with such a fixed specification of the volume of the blood treatment device 3000 the arterial line section 1 of the extracorporeal blood circuit 2000 may be emptied earlier or faster than the venous line section 3, it is in certain embodiments suggested to stop the blood pump 4000 before substitute liquid is conveyed across the venous addition point 7.

Such stopping of the conveying by the blood pump 4000 is in certain embodiments possible by the corresponding adjustment of the feed rate of the blood pump 4000, if the above-mentioned volume is known. Waiting for the moment in which the blood pump 4000 may be stopped—where applicable advantageously more precise—is also possible considering the signals of the arterial air bubble detector or optical sensor 11—if existent.

In some embodiments, the feed rate of the second conveying device 5000 is increased from the time of stopping the blood pump 4000 with the advantage of saving time.

If the volume of the utilized blood treatment device 3000 is known, the feed rate is advantageously set individually to the maximum possible feed rate with each reinfusion. This shortens the period of time the patient and the operating personnel have to spend at the blood treatment apparatus until the completion of this measure, due to the faster removal of blood from the extracorporeal blood circuit 2000.

The type of the utilized blood treatment device 3000 may be set by the operating personnel. Alternatively, the utilized type may be automatically determined by means of certain parameters which can be observed when filling the blood treatment device 3000.

If the volume of the blood treatment device 3000 is known, in some embodiments, the feed rate of the second conveying device 5000 is set such that at the point of introduction of the venous addition point 7 (or at a comparable point in the blood circuit) substitute and blood of the same dilution degree from both line sections 1, 3 meet at the same time.

The blood pump 4000 may subsequently either be stopped; alternatively, it continues to run.

In embodiments in which the blood pump 4000 continues to run, the arterial line section 1 of the extracorporeal blood circuit 2000 is advantageously comparatively flushed better; in embodiments in which the blood pump 4000 is stopped, the blood treatment device 3000 is advantageously comparatively flushed better.

In certain embodiments, the individual setting of the feed rates takes place according to the above-named formula (II) and (III) if necessary.

FIG. 2 shows pressure and volume progresses (y-axis, vertical) over the time (x-axis, horizontal), which may occur or may be measured using the arrangement shown in FIG. 1 while performing an embodiment of the method.

The scale on the left indicates a volume in ml/min for curves Q4000 and Q5000, the scales on the right indicate pressure in mmHg and apply for curves P_art for the arterial pressure progress and P_ven for the venous pressure progress, as well as for P_ven_sm, the calculated smoothed progress of the curve P_ven.

FIG. 2 shows a curve Q5000 which is indicated by the conveying volume of the second conveying device 5000 over the time t or the feed rate Q5000. The curve Q5000 is composed of several curve sections Q5000-1 to Q5000-5.

Q5000 shows the conveying line of the second conveying device 5000 during an optional, so-called free rinsing of the pre-dilution valve 33. The conveying line of the second conveying device 5000 which is applied for this purpose, is, based on 0 ml/min, e.g. 100 ml/min. After completion of this free rinsing, the feed capacity may optionally drop to 0 ml/min. The volume conveyed thereby may be 10 ml for example.

Q5000 indicates the feed capacity during the blood-return or emptying. Q5000 has a purely exemplary increasing course in the form of staircase, which however must not be neither in a form of a staircase nor must it comprise the pitches and heights. Q5000-2 shows the gradually increasing conveying capacity Q5000_actual of the second conveying device 5000 which is being successively increased by the control device according to the above formula II.

The increase of Q5000, i.e. the section Q5000-2, starts at the time t=0.

The progress section Q5000 goes in the present example at a time t=1 over a section Q5000-3 presently further increasing. The duration of the section Q5000-3 is thus T=(t=1)−(t=0).

The feed capacity Q5000 of the second conveying device 5000 increases from the time t=1 until reaching a specified maximum feed capacity Q5000-4, presently for example 300 ml/min, again in a staircase form.

The maximum feed capacity Q5000-4 may again be reached in steps or staircase form, as exemplary shown in FIG. 2. It may however be reached in a vertical increase (with reference to FIG. 2) or in some other way.

Starting from the time t=1, an increase of Q5000 without considering the arterial pressure is undertaken. The formulas II and III are not considered any further starting from t=1. The increase takes placed from t=1 regardless of the arterial pressure.

After the maximum feed capacity Q5000-4 has been reached and held, the curve Q5000 drops in its section Q5000-5 at the time t=2 to 0 ml/min. The method is concluded at t=2.

FIG. 2 shows further a curve Q4000 which indicates the feed volume of the blood pump 4000 through the time or the feed rate Q4000. The curve Q4000 is formed of several curve sections Q4000-1 to Q4000-4.

Q4000 shows the set feed capacity and—duration during an optional connection test. The applied feed capacity is, based on 0 ml/min, e.g. 25 ml/min. After completion of this connection test the feed capacity may optionally drop to 0 ml/min.

Q4000-2 shows the feed capacity during the blood return or emptying. Q4000-2 shows an exemplary increasing progress in a form of a staircase which however must not be neither in a form of a staircase nor must it comprise the indicated width and heights of the steps. Q4000-2 shows the gradually increasing feed capacity of the blood pump 4000 which stands in fixed relation to the feed capacity of the second conveying device 5000.

The increase of Q4000, i.e. its section Q4000-2, begins at the time t=0.

The progress section Q4000-2 passes over at a time t=1 which is between t=0 and t=1 into a plateau, the section Q4000-3. This plateau may correspond to a specified maximum feed capacity of 100 ml/min by way of example.

The feed capacity of the blood pump 4000 drops at the time t=1 to 0 ml/min. The drop is denoted with Q4000-4. FIG. 2 shows further a pressure progress P_art, its scaling is represented on the right edge of FIG. 2 and namely on the left of both adjacent scales.

The pressure P_art, e.g. measured by the arterial pressure sensor 9 of FIG. 1, increases due to the conveyance by the blood pump 4000 starting from the time t=0. The local maximum values P_art-1, P_art-2 and so on denote, respectively, highest pressure which is measured in certain rotary angle by conveyance with the blood pump 4000 which is embodied as a roller pump. This maximum pressure occurs during the intrusion of the roll of the blood pump 4000 with the pump tubing segment. The maximum value is adjustable as FIG. 2 also shows. The last measured maximum value P_art-1, P_art-2, and so on, respectively, enter into controlling. In this way, a first maximum value P_art-1 which occurs immediately after the begin of the method is initially measured and used in the following example as basis for the calculation as P_art,scan.

The blood pump 4000 generates, design-limited, two pressure pulses per rotation (may be more than two in other designs) which are measured at the arterial pressure sensor 9. An algorithm present in the control device determines, by means of the rotation angle of the pump rotor and of the actual pressure present at the pressure sensor, these maximum pressures P_art-1, P_art-2 and so on respectively, and provides this pressure for further processing as P_art, scan as described above.

The blood return begins at t=0, when the second conveying device 5000 preferably at the same time as the blood pump 4000 begins conveying, optionally with the lowest possible rate (the downward limitation is hereby design-limited), in this case 25 ml/min.

Until the time t=1 both the second conveying device 5000 as well as the blood pump 4000 convey.

Thereby the blood pump 4000 is always regulated such that to convey with only a fraction of the feed rate Q5000 of the second conveying device 5000. The exemplary selected relation in this case is Q4000=Q5000*0.82. This value has proven itself particularly advantageous due to the fact that with it, the passing of blood clots from the entry of the blood treatment device, here as a dialyser, on its blood side in the arterial line section 1 is prevented.

It may therefore be intended that starting from a conveyance Q5000 of the second conveying device 5000 of e.g. more the 122 ml/min, the feed rate Q4000 of the blood pump 4000 is limited to e.g. 100 ml/min.

Following each created positive pressure pulse P_art, scan by the blood pump 4000 which is measured in the pressure sensor 9, the feed rate Q5000 of the second conveying device 5000 is increased. It is increased to an upper point which is determined by the user by means of the maximum measurement range limit of the pressure sensor where a specified pressure limit P_art,target is reached.

Therefore, the pressure in the pressure sensor 9 shall reliably not exceed its upper measurement range P_art,max, here 455 mmHg in the present example. P_art,max is in this example, the pressure value starting from which the pressure sensor releases an alarm due to high pressure. Hence, the regulation target P_art,target for the pressure in the pressure sensor 9 is specified to be 90% of the measurement range*0.9, i.e. around 410 mmHg.

In the example of FIG. 2, the first maximum value for the pressure, namely P_art-1 is about 260 mmHg. If measured to the target value P_art,target of about 410 mmHg (corresponds to 455 mmHg.*0.9), the control difference in this example is now about 150 mmHg.

The feed rate Q5000 of the second conveying device 5000 is increased in the section Q5000-2 as follows:

$$Q5000\_future = Q5000\_actual + ((P\_art,target)-(P\_art,scan))+0.12 * ml/min$$

Q5000_future is thereby the new feed rate to be determined. Q5000_actual is the last determined. Q5000_future might therefore also be denoted as Q5000(t=x+1) and Q5000_actual might be denoted as Q5000(t=x).

Should the pressure in the pressure sensor 9 exceed the regulation target P_art,target, the following countermeasures are taken:

$$Q5000\_future = Q5000\_actual + ((P\_art,target)-(P\_art,scan))*0.24*ml/min$$

Starting form the time t=1 of FIG. 2, the blood pump 4000 ceases to convey, only the second conveying device 5000 still coveys.

Starting from the time t=1 of FIG. 2, the feed rate Q5000 of the second conveying device 5000, presently purely by way of example, is increased each 0.5 s of 10 ml/min until the maximum flow which is determined by the user in the device is reached. Other values are of course encompassed by the present invention as well.

The progress P_ven is measured by means of the venous pressure sensor, the course P_ven_sm corresponds to the smoothing of the first-mentioned.

| Reference Numerals List | |
|---|---|
| Reference numerals | Description |
| 1000 | functional device |
| 2000 | extracorporeal blood circuit |
| 3000 | blood treatment device |
| 4000 | blood pump |
| 5000 | second conveying device |
| 1 | arterial line section |
| 3 | venous line section |
| 5 | arterial needle connection |
| 7 | venous addition point |
| 9 | (arterial) pressure sensor or pressure measurement |
| 11 | arterial clamp |
| 13 | arterial septum |
| 15 | venous air bubble detector/optical sensor |
| 17 | venous clamp |
| 19 | venous needle |
| 21 | venous patient connector |
| 23 | venous septum |
| 24 | check valve |
| 25 | heparin syringe |
| 27 | arterial air bubble detector/optical sensor |
| 29 | single needle chamber |
| 29a | blood chamber or bubble chamber |
| 31 | clot catcher |
| 33 | pre-dilution valve |
| P_art | |
| P_art-1, -2, -3 | maximum value P_art, scan |
| P_ven | venous pressure |
| P_ven_sm | smoothed progress of the curve P_ven |
| Q4000 | feed rate of the blood pump |
| Q4000-1 to Q4000-4 | sections of curve Q4000 |

-continued

| Reference Numerals List | |
|---|---|
| Reference numerals | Description |
| Q5000 | feed rate of the second conveying device |
| Q5000-1 to Q5000-5 | sections of curve Q5000 |

The invention claimed is:

1. A method of removing blood from an extracorporeal blood circuit connected with a blood treatment apparatus after concluding a blood treatment of a patient, the method comprising:
 operating a substitute pump of the blood treatment apparatus at a feed rate to introduce a substituate liquid into the extracorporeal blood circuit at a location of a pre-dilution valve,
 the extracorporeal blood circuit comprising an arterial line in which, during the blood treatment of the patient, blood from the patient flows toward a blood treatment device and a venous line in which treated blood from the blood treatment device flows back toward the patient; and
 while operating the substitute pump to introduce the substituate liquid into the extracorporeal blood circuit, operating a blood pump of the blood treatment apparatus at a feed rate in a second conveying direction to convey blood within the extracorporeal blood circuit, the second conveying direction being opposite to a first conveying direction in which the blood pump is customarily operated during the blood treatment, and
 wherein the blood pump is a roller pump and the feed rate of the blood pump is regulated at 75% to 90% of the feed rate of the substitute pump such that blood clots, that may have formed in the extracorporeal blood circuit between the pre-dilution valve and the blood treatment device during the blood treatment of the patient, are prevented from entering the venous line,
 wherein the feed rate of the blood pump and the feed rate of the substitute pump during the removal of blood from the extracorporeal blood circuit are monitored or controlled or regulated by determining a difference between an actual feed pressure of the blood pump and a target feed pressure of the blood pump, and by increasing the feed rate of the blood pump based on the determined difference between the actual feed pressure of the blood pump and the target feed pressure of the blood pump, and
 wherein the actual feed pressure of the blood pump is measured or calculated when a pre-determined rotation angle of a pump rotor of the blood pump is reached.

2. The method according to claim 1, wherein the feed rate of the blood pump is 80% to 84% of the feed rate of the substituate pump.

3. The method according to claim 1, wherein the extracorporeal blood circuit is partially formed by a blood cassette.

4. The method according to claim 1, wherein the blood treatment device is a dialyzer.

5. The method according to claim 1, wherein the feed rate of the blood pump is limited to 90 to 110 ml/min.

6. The method according to claim 5, wherein the feed rate of the blood pump is set by a user.

7. The method according to claim 1, further comprising measuring the actual feed pressure of the blood pump using an arterial pressure sensor of the blood treatment apparatus.

8. The method according to claim 1, wherein the feed rate of the blood pump and/or the feed rate (Q5000) of the substituate pump is not further increased after the actual feed pressure has reached or exceeded the target feed pressure, wherein the target feed pressure is determined as follows:

$$P\_art,target = a*P\_art,max$$

where:
 $P\_art,target$ is the target feed pressure;
 $a$ is a constant between 0.85 and 0.95;
 $P\_art,max$ is a pre-set or specified measurement range limit or an admissible maximum value for a pressure measured by an arterial pressure sensor.

9. The method according to claim 1, further comprising: increasing the feed rate of the substituate pump according to the formula:

$$Q5000\_future = Q5000\_actual + ((P\_art,target) - (P\_art,scan))*b;$$

where:
 $Q5000\_future$ is a feed rate of the substituate pump which is to be set henceforth to a point of time $t\_future$;
 $Q5000\_actual$ is an actual feed rate of the substituate pump at a point of time $t\_actual$, which is to be replaced by $Q5000\_future$ and precedes this temporally, wherein $t\_actual$ comes before $t\_future$; $t\_future$ may be denoted as $t(x+1)$ and $t\_actual$ as $t(x)$;
 $P\_art,target$ is a pre-set target value which should be detected by an arterial pressure sensor;
 $P\_art,scan$ is a pressure value which is measured by the arterial pressure sensor during adapting of the actual feed rate $Q5000\_actual$; and
 $b$ is a constant between 0.10 and 0.15.

10. The method according to claim 1, further comprising: decreasing the feed rate of the substituate pump when the actual feed pressure of the blood pump reaches the target feed pressure of the blood pump or exceeds it, according to the formula:

$$Q5000\_future = Q5000\_actual + ((P\_art,target) - (P\_art,scan))*c;$$

where:
 $Q5000\_future$ is a feed rate of the substituate pump which is to be set henceforth to a point of time $t\_future$;
 $Q5000\_actual$ is an actual feed rate of the substituate pump at a point of time $t\_actual$, which is to be replaced by $Q5000\_future$ and precedes this temporally, wherein $t\_actual$ comes before $t\_future$; $t\_future$ may be denoted as $t(x+1)$ and $t\_actual$ as $t(x)$;
 $P\_art,target$ is a pre-set target value which should be detected by an arterial pressure sensor
 $P\_art,scan$ is a pressure value which is measured by the arterial pressure sensor during the adapting of the actual feed rate_$Q5000\_actual$; and
 $c$ is a constant between 0.20 and 0.30.

11. The method according to claim 1, further comprising: stopping the blood pump before substituate liquid is introduced into the venous line of the extracorporeal blood circuit at a venous addition point or before substituate liquid reaches a point at which fluid from the venous line and fluid from the arterial line meet.

12. The method according to claim 1, further comprising:
stopping the substitute pump before substitute liquid is introduced into the venous line of the extracorporeal blood circuit at a venous addition point, or before substitute liquid reaches a point at which fluid from the venous line section and fluid from the arterial line meet.

13. The method according to claim 1, further comprising:
checking a connection of an arterial needle connection of the extracorporeal blood circuit with a venous addition point of the extracorporeal blood circuit.

14. The method according to claim 13, wherein checking the connection comprises:
creating a pressure balance or compensation;
detecting a diastolic patient pressure; and
building up a negative pressure by operating the blood pump in the first conveying direction.

15. The method according to claim 13, wherein the venous addition point of the extracorporeal blood circuit leads into the venous line upstream of a blood chamber and upstream of a clot catcher.

16. A blood treatment apparatus control device arranged and/or configured to execute the method according to claim 1.

17. A computer program product with a program code saved on a machine-readable medium for causing a blood treatment apparatus to carry out the method according to claim 1 when the computer program product runs on a computer.

* * * * *